(12) United States Patent
Sugiyama

(10) Patent No.: US 6,340,596 B1
(45) Date of Patent: Jan. 22, 2002

(54) REAGENT COMPOSITION FOR MEASURING HYDROGEN SULFIDE AND METHOD FOR MEASURING HYDROGEN SULFIDE

(75) Inventor: Masami Sugiyama, Tokyo (JP)

(73) Assignee: Fujirebio Inc., Tokyo (JP)

( * ) Notice: Subject to any disclaimer, the term of this patent is extended or adjusted under 35 U.S.C. 154(b) by 0 days.

(21) Appl. No.: 09/248,316

(22) Filed: Feb. 11, 1999

(30) Foreign Application Priority Data

Feb. 12, 1998 (JP) ............................................ 10-044300

(51) Int. Cl.$^7$ ............................................... G01N 33/00
(52) U.S. Cl. ........................ 436/121; 436/119; 436/120
(58) Field of Search ................................. 436/119–121

(56) References Cited

U.S. PATENT DOCUMENTS

| | | | | |
|---|---|---|---|---|
| 3,929,404 A | * | 12/1975 | Kalopissis et al. | 8/407 |
| 4,829,047 A | * | 5/1989 | Niwa et al. | 503/227 |
| 5,985,540 A | * | 11/1999 | Tan et al. | 435/4 |
| 5,998,191 A | * | 12/1999 | Tan et al. | 435/232 |

FOREIGN PATENT DOCUMENTS

| | | | |
|---|---|---|---|
| EP | 243125 | * | 10/1987 |
| GB | 811679 | * | 4/1959 |
| GB | 1193923 | * | 6/1970 |
| GB | 1235892 | * | 11/1971 |
| GB | 2083488 | * | 3/1982 |
| JP | 53-9519 | * | 1/1978 |
| JP | 59-126245 | * | 7/1984 |

OTHER PUBLICATIONS

M. Kamaya et al, Kogakuin Daigaku Kenkyu Hokoku 1993, 74, 101–104.*
T. D. Rees et al, Analyst 1971, 96, 201–208, Mar. 1971.*
K. Toei et al, Analytica Chinica Acta 1977, 90, 319–322, May 1977.*
W. J. Kirsten CHem. Abstr. 1979, 90, abstract 47863g, Feb. 1979.*
W. Davidson et al, Anaylst 1983, 108, 1235–1239, Oct. 1983.*
C. F. Wood et al, Analyst 1988, 113, 1635–1638, Nov. 1988.*
M. Kamaya et al, Chem. Abstr. 1994, 120, abstract 314589n, Jun. 1994.*
J. V. Das et al, Chem. Abstr. 1995, 122, abstract 285838b, Jun. 1995.*
K. Hofmann et al, Fresenius Z. Anal. Chem. 1967, 232, 167–172.*
S. Morohashi et al. Yamagata Daigaku Kiyo, Kogaku Jan. 1970, 11, 287–298.*
R. C. Baetzold et al, J. Am. Chem. Soc. Mar. 1971, 93, 1347–1353.*
D. F. Adams Health Lab. Sci. Oct. 1975, 12, 362–368.*
Z. Holzbecher et al, Sb. Vys. Sk. Chem.–Technol. Praze, Anal. Chem. 1977, H12, 75–87.*
M. B. Kloster et al, J. –Am. Water Works Assoc. Oct. 1977, 69, 544–546.*
D. J. Leggett et al, Anal. Chim. Acta 1981, 128, 163–168.*
M. A. Abdalla et al, Analyst Feb. 1982, 107, 213–217.*
U. Nickel et al, Ber. Bunsen–Ges. Phys. Chem. 1985, 89, 999–1004.*
W. Lei et al, Anal. Chim. Acta 1989, 226, 165–170.*
T. Stan, et al., Farmacia, vol. 27, No. 2, pp. 85–89, "O Noua Metoda Spectrofometrica, Pentru Determinarea Hidrogenului Sulfurat Din Aer", 1979.
M. Krihak, et al., SPIE, vol. 2293, pp. 88–98, "Active Sol–Gel Materials for Fiber Optic Chemical Sensors", 1994.
Oliver Kohls, et al, SPIE, vol. 2836, pp. 311–321, "Thionine as an Indicator for Use as a Hydrogen Sulfide Optode", 1996.
Uzer M. Noor, et al., Journal of Sol–Gel Science and Technology, vol. 11, pp. 177–183, "Sol–Gel Derived Thin Films for Hydrogen Sulphide Gas Sensing", 1998.
Lilly Gustafsson, Talanta, vol. 4, pp. 227–235, "Determination of Ultramicro Amounts of Sulphate as Methylene Blue–I", 1960.
N. A. Matheson, Analyst, vol. 99, pp. 577–579, "Modified Methylene Blue Method for the Micro–Determination of Hydrogen Sulphide", Sep., 1974.

* cited by examiner

*Primary Examiner*—Arlen Soderquist
(74) *Attorney, Agent, or Firm*—Oblon, Spivak, McClelland, Maier & Neustadt, P.C.

(57) ABSTRACT

A reagent composition for measuring hydrogen sulfide, which comprises an aniline derivative represented by the general formula (I):

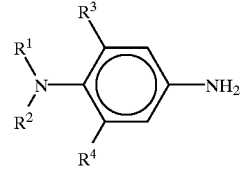

wherein $R^1$ and $R^2$ independently represent a substituted or unsubstituted $C_2$–$C_6$ alkyl group, and $R^3$ and $R^4$ independently represent a hydrogen atom, a $C_1$–$C_6$ alkyl group or a halogen atom; and an oxidizing agent, as well as a method for measuring hydrogen sulfide in a sample using the aniline derivative represented by the general formula (I) above.

20 Claims, 4 Drawing Sheets

REAGENT COMPOSITION FOR MEASURING HYDROGEN SULFIDE AND METHOD FOR MEASURING HYDROGEN SULFIDE

FIELD OF THE INVENTION

The present invention relates to a reagent composition for measuring hydrogen sulfide and a method for measuring hydrogen sulfide by using the reagent composition, which reagent composition comprising a specific aniline derivative and an oxidizing agent.

BACKGROUND OF THE INVENTION

Hydrogen sulfide is colorless gas with a rancid smell which occurs naturally in volcanic gases, mineral springs, etc. and is also produced from rotten sulfur-containing proteins. Hydrogen sulfide is industrially present in exhaust gas and waste liquid from factories, etc. Hydrogen sulfide released in the air can sometimes be oxidized to sulfurous acid gas. Hydrogen sulfide and sulfurous acid gas are harmful to a human body. Sulfurous acid gas is a cause of acid rain and is problematical for the environment. The concentrations of these gases are therefore regulated. From this viewpoint, it is beneficial to healthy life to measure the hydrogen sulfide concentration in the air, rivers, soil, and exhaust gas or waste liquid from factories.

As described above, measurement of hydrogen sulfide is environmentally useful and various methods have been used for determining the hydrogen sulfide concentration. For example, methods using a lead acetate paper strip or a lead acetate detector tube and colorimetric methods, such as iodometry and a Methylene Blue method, (see Talenta, No. 4, p. 227 (1960)) are known.

However, the conventional methods for measuring hydrogen sulfide in the air, exhaust gas, or waste liquid require a large quantity of a sample due to insufficient detection sensitivity, which makes the sampling operation troublesome. Accordingly, an object of the present invention is to provide a method for measuring hydrogen sulfide which are simpler and yet more sensitive than conventional methods or determining hydrogen sulfide.

SUMMARY OF THE INVENTION

As a result of extensive studies, the inventor of the present invention found that hydrogen sulfide concentration can be determined simply and with high sensitivity by using the aniline derivative represented by the general formula (I), resulting in accomplishment of the present invention.

Thus, the present invention provides a reagent composition for measuring hydrogen sulfide, which comprises an aniline derivative represented by the general formula (I):

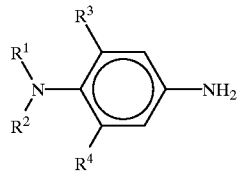

wherein $R^1$ and $R^2$ independently represent a substituted or unsubstituted $C_2$–$C_6$ alkyl group, and $R^3$ and $R^4$ independently represent a hydrogen atom, a $C_1$–$C_6$ alkyl group or a halogen atom; and an oxidizing agent.

The present invention also provides a method for measuring hydrogen sulfide, which can be considered as an improved Methylene Blue method, which comprises reacting the aniline derivative represented by the general formula (I) above and an oxidizing agent with hydrogen sulfide in a solution under an acidic condition, and colorimetrically analyzing the resulting solution.

DETAILED DESCRIPTION OF THE INVENTION

Figure 1:
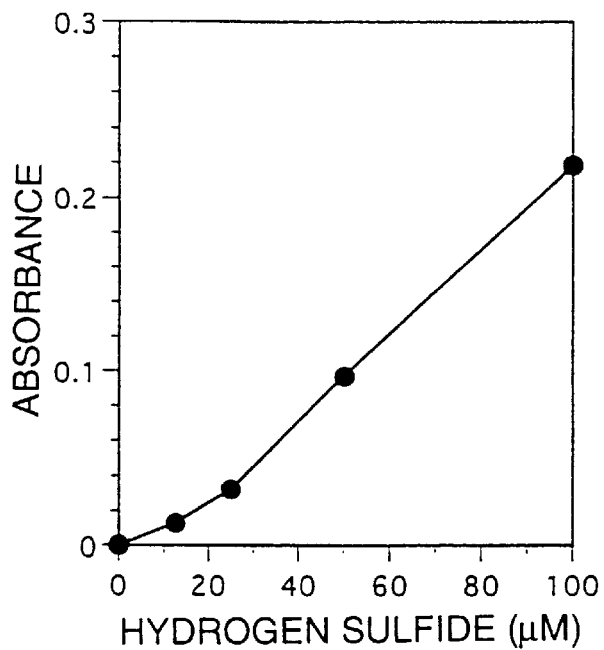
FIG. 1 shows the result of hydrogen sulfide measurement by the conventional Methylene Blue method.

The hydrogen sulfide measuring method of the present invention comprises reacting the aniline derivative of the general formula (I) above and an oxidizing agent with hydrogen sulfide in a solution under an acidic condition, and colorimetrically analyzing the resulting solution.

$R^1$ or $R^2$ in the general formula (I) above is a substituted or unsubstituted linear or branched $C_2$–$C_6$ alkyl group, and a substituted or unsubstituted linear or branched $C_3$–$C_4$ alkyl group is preferable for the highly sensitive measurement of hydrogen sulfide and reduction in the measurement time. Examples of the $C_2$–$C_6$ alkyl group include an ethyl group, a propyl group, a butyl group, a pentyl group, a hexyl group, an isopropyl group, an isobutyl group, and the like. Examples of the substituent of the substituted $C_2$–$C_6$ alkyl group includes a sulfo group, a sulfonate group, a carbamoyl group, a substituted amino group, and the like. The number of substituents of the substituted $C_2$–$C_6$ alkyl group is not particularly limited and it is generally from 1 to 4 and preferably from 1 to 2.

The substituted amino group means a primary or secondary amino group substituted with $C_1$–$C_6$ alkyl group(s) Examples of the substituted amino group include a methylamino group, an ethylamino group, a propylamino group, a butylamino group, a pentylamino group, a hexylamino group, a dimethylamino group, a diethylamino group, a dipropylamino group, and the like.

$R^3$ or $R^4$ in the general formula (I) above is a hydrogen atom, a linear or branched $C_1$–$C_6$ alkyl group, or a halogen atom. Examples of the $C_1$–$C_6$ alkyl group include a methyl group, an ethyl group, a propyl group, a butyl group, a pentyl group, a hexyl group, an isopropyl group, an isobutyl group, and the like. Examples of the halogen atom include a fluorine atom, a chlorine atom, a bromine atom, and iodine atom.

Illustrative examples of the aniline derivative represented by the general formula (I) above includes p-aminodiethylaniline, p-aminodipropylaniline, p-aminodibutylaniline, p-aminodipentylaniline, p-aminodihexylaniline, p-aminodi(3-sulfopropyl)aniline, 4-amino-N,N-bis[2-(N',N'-dimethylamino)ethyl]aniline, 4-amino-N,N-bis[2-(N',N'-diethylamino)ethyl]aniline, 4-amino-2,6-dibromo-N,N-diethylaniline, 4-amino-2,6-dibromo-N,N-dipropylaniline, 4-amino-2,6-dichloro-N,N-diethylaniline, 4-amino-2,6-dichloro-N,N-dipropylaniline. While these reagents are easily available, they can also be prepared easily from p-nitroaniline, etc. by alkylation, reduction, and the like.

Examples of the oxidizing agent, which is the other component of the reagent composition of the present invention, includes ferric chloride, potassium ferricyanide, ammonium persulfate and potassium persulfate.

In the measurement method of the present invention, the aniline derivative of the general formula (I) above is preferably used in the form of, for example, a 0.1 to 10 mM, preferably 0.5 to 5 mM, aqueous solution and is added in an excess amount (generally in an amount of from 10 $\mu$M to 500 $\mu$M, preferably from 20 $\mu$M to 200 $\mu$M) to a sample solution containing hydrogen sulfide. It is preferable to add an acid (preferably, a mineral acid such as hydrochloric acid or sulfuric acid) to the reaction solution to carry out the reaction under an acidic condition (generally at pH 2.5 or less, preferably at pH 2 or less). The amount of the acid is not particularly limited as long as the acidic condition described above can be achieved. The acid can be used in the form of, for example, a 100 mM to 5M, preferably 150 mM to 600 mM, aqueous solution. The oxidizing agent is preferably used in the form of, for example, a 0,2 mM to 8 mM, preferably 0.5 mM to 4 mM, aqueous solution and is added in an excess amount (generally in an amount of from 50 $\mu$l to 400 $\mu$l, preferably from 100 $\mu$l to 300 $\mu$l) to the reaction solution. The temperature for the reaction is not particularly limited, but the reaction is carried out generally from room temperature (i.e., about 18° C. to about 28° C.) to around 50° C.

The aniline derivative of the general formula (I) above, a sample containing hydrogen sulfide, an acid, and an oxidizing agent can be mixed in an arbitrary order, as long as the reaction can sufficiently proceed. It is preferable to first add the aniline derivative and an acid to the sample, and then add an oxidizing agent. In addition, it is also possible to first add the aniline derivative to the sample and then add a mixture of an acid and the oxidizing agent. The aniline derivative, an acid, and an oxidizing agent may be provided as separated reagents in a kit, or any two or more of them can be provided as a-mixed reagent in a kit.

Before carrying out the measurement, it is preferred to first determine the maximum absorption wavelength of the colorant produced by the reaction of the aniline derivative used, so that colorimetry is effected at that wavelength.

The measuring method of the present invention is generally applied to measurement of hydrogen sulfide in a solution. In addition, for measuring hydrogen sulfide in the air, for example, hydrogen sulfide may be reacted with a metal such as sodium, iron, cobalt, cadmium, silver or zinc or an amine derivative thereof, and the resulting sulfide or complex is measured by the method of the present invention (see, *Analyst:,* Sept. 1974, Vol. 99, p. 577–579).

The measuring method of the present invention can determine even a trace amount of hydrogen sulfide resulting from enzymatic decomposition of sulfur-containing amino acids in vivo and, therefore, it is applicable to measurement of biological components, etc.

The reagent composition of the present invention may further contain other components such as a stabilizing agent (e.g., cyclodextrin, partial methylated cyclodextrin, etc.).

The present invention will now be illustrated in greater detail with reference to Reference Examples and Examples.

Unless otherwise indicated, all parts, ratios, percentages, and the like in this specification are by weight.

REFERENCE EXAMPLE 1

Measurement of Hydrogen Sulfide by Methylene Blue Method

To 10 ml of a 0.5 g/dl aqueous solution of zinc acetate was added 2 ml of a 12.5, 25, 50 or 100 $\mu$M sodium sulfide aqueous solution. To the resulting solution was added 4 ml of a 75 mg/dl solution of p-aminodimethylaniline in 4N sulfuric acid solution, and the mixture was allowed to stand for 5 minutes. Thereafter, 1 ml of a 1.2 g/dl solution of ferric chloride in 0.015 M sulfuric acid solution was added. After allowing the mixture to stand for 5 minutes, the absorbance of the mixture at a wavelength of 665 nm was determined to measure hydrogen sulfide. As a control, the measurement was repeated in the same manner but using an aqueous solution containing no sodium sulfide. The result is shown in FIG. 1.

Example 1

Measurement of Hydrogen Sulfide Using p-aminodiethylaniline

Figure 2:
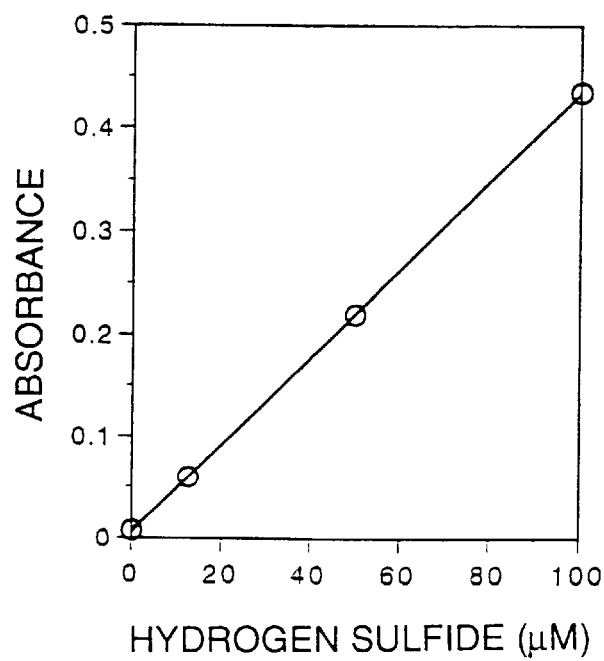
FIG. 2 shows the result of hydrogen sulfide measurement using p-aminodiethylaniline.

To 1 ml of an aqueous solution containing 1 mM p-aminodiethylaniline was added 50 $\mu$l of 1N hydrochloric acid, and 200 $\mu$l of a sample containing 12.5, 25, 50 or 100 $\mu$M sodium sulfide was added thereto. To the solution was further added 200 $\mu$l of a 10 mM potassium ferricyanide aqueous solution, and the mixture was kept at 37° C. for 10 minutes. The absorbance of the mixture at a wavelength of 672 nm was determined to measure hydrogen sulfide. As a control, the measurement was repeated in the same manner but using an aqueous solution containing no sodium sulfide. The result is shown in FIG. 2.

Example 2

Measurement of Hydrogen Sulfide Using p-aminodi(3-sulfopropyl)aniline

Figure 3:
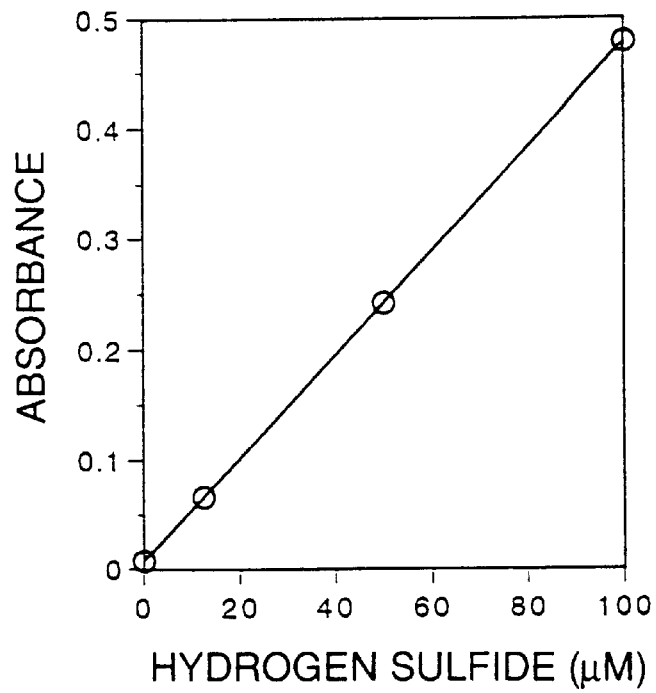
FIG. 3 shows the result of hydrogen sulfide measurement using p-aminodi(3-sulfopropyl)aniline.

To 1 ml of an aqueous solution containing 1.5 mM p-aminodi(3-sulfopropyl)aniline was added 50 $\mu$l of 1N hydrochloric acid, and 200 $\mu$l of a sample containing 25, 50 or 100 $\mu$M sodium sulfide was added thereto. To the solution was further added 100 $\mu$l of a 10 mM potassium ferricyanide aqueous solution, and the mixture was kept at 37° C. for 10 minutes. The absorbance of the mixture at a wavelength of 675 nm was determined to measure hydrogen sulfide. As a control, the measurement was repeated in the same manner but using an aqueous solution containing no sodium sulfide. The result is shown in FIG. 3.

Example 3

Measurement of Hydrogen Sulfide Using p-aminodipropylaniline

Figure 4:
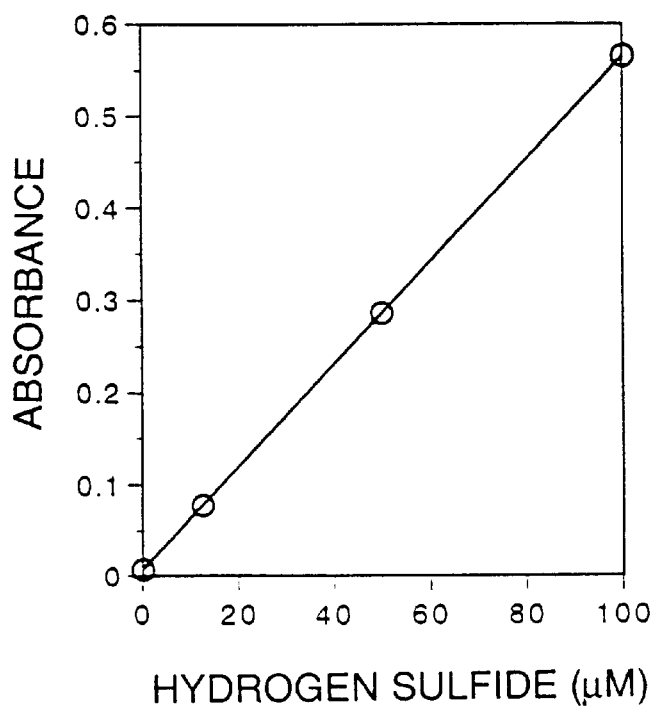
FIG. 4 shows the result of hydrogen sulfide measurement using p-aminodipropylaniline.

To 1 ml of an aqueous solution containing 1.5 mM p-aminodipropylaniline was added 50 $\mu$l of 1N hydrochloric acid, and 200 $\mu$l of a sample containing 25, 50 or 100 $\mu$M sodium sulfide was added thereto. To the solution was further added 100 $\mu$l of a 10 mM potassium ferricyanide aqueous solution, and the mixture was kept at 37° C. for 10 minutes. The absorbance of the mixture at a wavelength of 675 nm was determined to measure hydrogen sulfide. As a control, the measurement was repeated in the same manner but using an aqueous solution containing no sodium sulfide. The result is shown in FIG. 4.

Example 4

Measurement of Hydrogen Sulfide Using p-aminodibutylaniline

Figure 5:
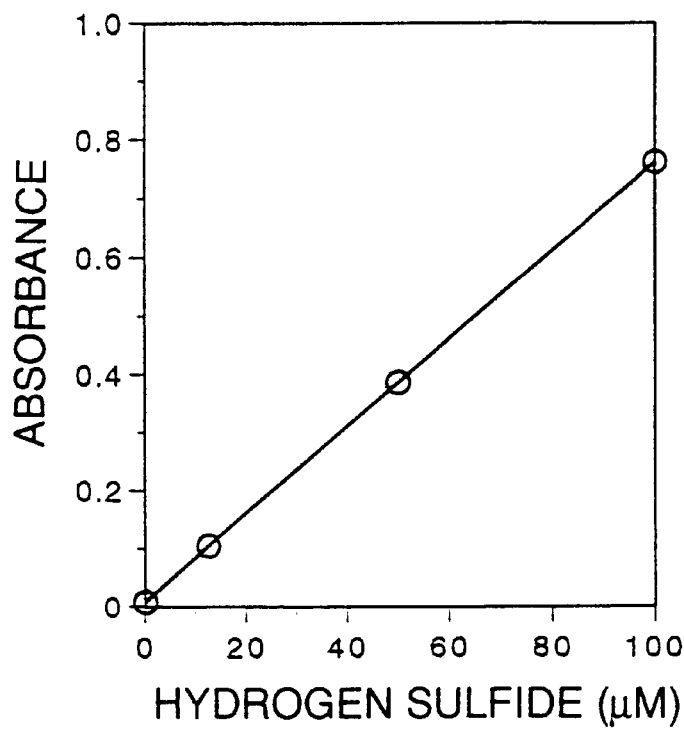
FIG. 5 shows the result of hydrogen sulfide measurement using p-aminodibutylaniline.

To 1 ml of an aqueous solution containing 1.5 mM p-aminodibutylaniline was added 50 μl of 1N hydrochloric acid, and 200 μl of a sample containing 25, 50 or 100 μM sodium sulfide was added thereto. To the solution was further added 100 μl of a 10 mM potassium ferricyanide aqueous solution, and the mixture was kept at 37° C. for 10 minutes. The absorbance of the mixture at a wavelength of 680 nm was determined to measure hydrogen sulfide. As a control, the measurement was repeated in the same manner but using an aqueous solution containing no sodium sulfide. The result is shown in FIG. 5.

Example 5

Figure 6:
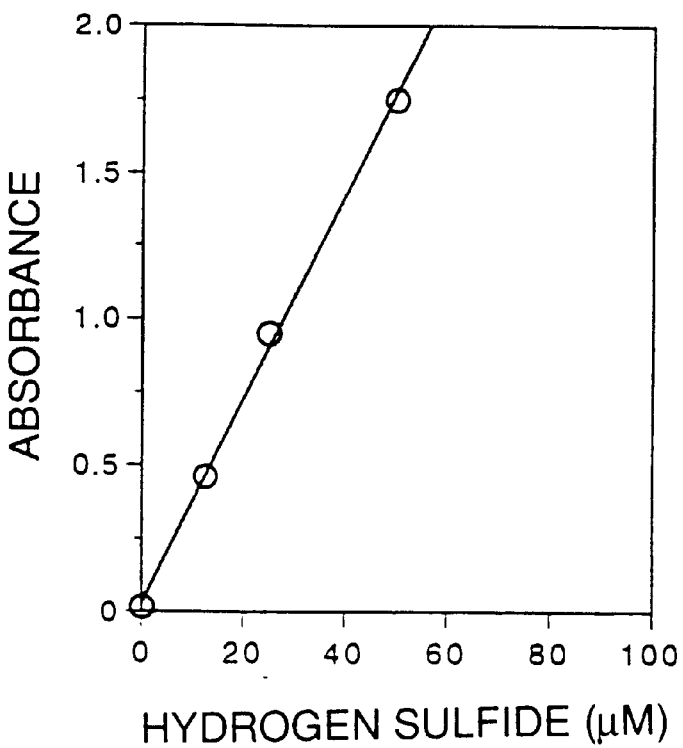
FIG. 6 shows the result of hydrogen sulfide measurement using 4-amino-N,N-bis[2-(N',N'-diethylamino)ethyl]aniline.

Measurement of Hydrogen Sulfide Using 4-amino-N,N-bis[2-(N',N'-diethylamino)ethyl]aniline To 1 ml of an aqueous solution containing 1.5 mM 4-amino-N,N-bis[2-(N',N'-diethylamino)ethyl]aniline was added 50 μl of 1N hydrochloric acid, and 100 μl of a sample containing 12.5, 25, or 50 μM sodium sulfide was added thereto. To the solution was further added 200 μl of a 10 mM potassium ferricyanide aqueous solution, and the mixture was kept at 37° C. for 10 minutes. The absorbance of the mixture at a wavelength of 690 nm was determined to measure hydrogen sulfide. As a control, She measurement was repeated in the same manner but using an aqueous solution containing no sodium sulfide. The result is shown in FIG. 6.

Example 6

Figure 7:
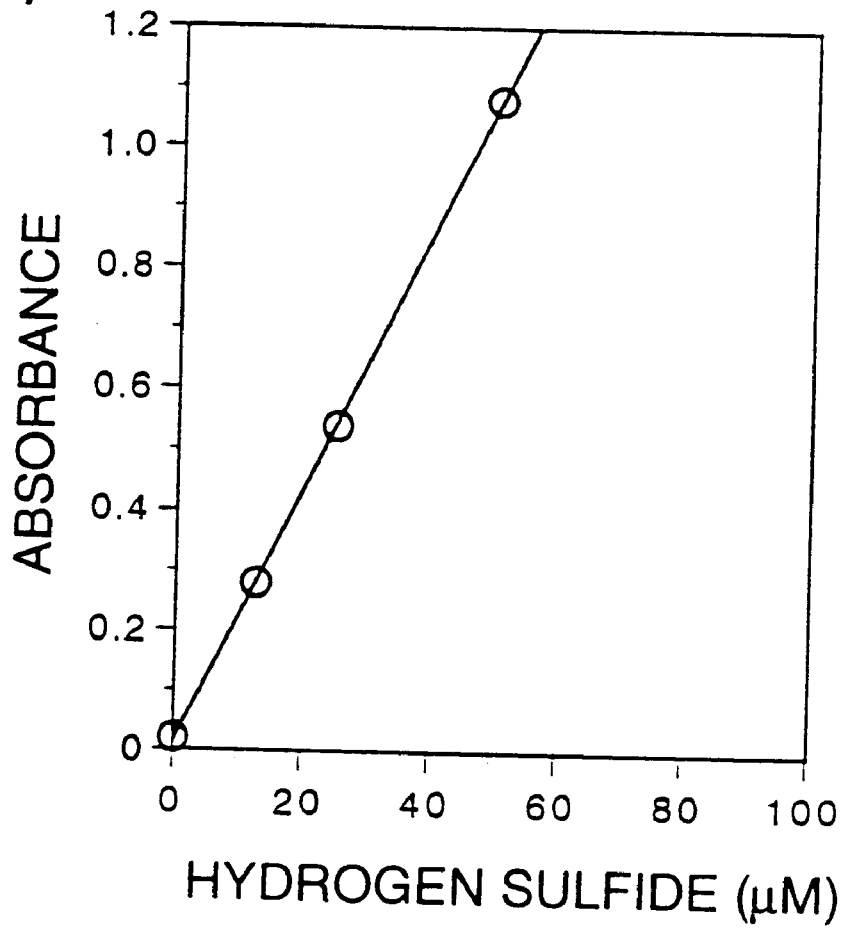
FIG. 7 shows the result of hydrogen sulfide measurement using 4-amino-2,6-dibromo-N,N-dipropylaniline.

Measurement of Hydrogen Sulfide Using 4-amino-2,6-dibromo-N,N-dipropylaniline, dipropylaniline The measurement was repeated in the same manner as described in Example 5, except that 1 ml of an aqueous solution containing 1.5 mM 4-amino-2,6-dibromo-N,N-dipropylaniline was used. As a control, the measurement was repeated in the same manner but using an aqueous solution containing no sodium sulfide. The result is shown in FIG. 7.

According to the present invention, hydrogen sulfide contained in a sample in a trace amount can be detected simply and with high sensitivity by using the aniline derivative represented by the general formula (I) above as the reagent. The method of the present invention achieves 2 to 18 times higher sensitivity than that of the conventional Methylene Blue method.

While the invention has been described in detail and with reference to specific embodiments thereof, it will be apparent to one skilled in the art that various changes and modifications can be made therein without departing from the spirit and scope thereof.

This application is based on Japanese patent application No. Hei-10-44300, filed on Feb. 12, 1998, and incorporated therein by reference.

What is claimed is:

1. A reagent composition suitable for measuring hydrogen sulfide, which comprises an aniline derivative represented by the general formula (I):

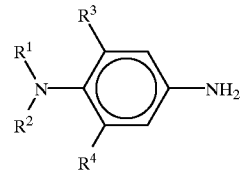

wherein $R^1$ and $R^2$ independently represent an unsubstituted $C_2-C_6$ alkyl group or a $C_2-C_6$ alkyl group substituted with at least one substituent each selected from the group consisting of a sulfo group, a sulfonate group, a carbamoyl group, and a substituted amino group, and $R^3$ and $R^4$ independently represent a hydrogen atom, a $C_1-C_6$ alkyl group or a halogen atom; and an oxidizing agent;
with the proviso that when one of $R^3$ and $R^4$ is a hydrogen atom, and the other of $R^3$ and $R^4$ is a hydrogen atom or a methyl group, $R^1$ and $R^2$ are each a substituted $C_2-C_6$ alkyl group.

2. The reagent composition according to claim 1, wherein said substituent is a substituted amino group.

3. The reagent composition according to claim 1, wherein said oxidizing agent is ferric chloride, potassium ferricyanide, ammonium persulfate or potassium persulfate.

4. The reagent composition according to claim 1, wherein the aniline derivative is p-aminodi(3-sulfopropyl)aniline.

5. The reagent composition according to claim 1, wherein the aniline derivative is 4-amino-N,N-bis[2-(N',N'-dimethylamino)ethyl]aniline.

6. The reagent composition according to claim 1, wherein the aniline derivative is 4-amino-N,N-bis[2-(N',N'-diethylamino)ethyl]aniline.

7. The reagent composition according to claim 1, wherein the aniline derivative is 4-amino-2,6-dibromo-N,N-diethylaniline.

8. The reagent composition according to claim 1, wherein the aniline derivative is 4-amino-2,6-dibromo-N,N-dipropylaniline.

9. The reagent composition according to claim 1, wherein the aniline derivative is 4-amino-2,6-dichloro-N,N-diethylaniline.

10. The reagent composition according to claim 1, wherein the aniline derivative is 4-amino-2,6-dichloro-N,N-dipropylaniline.

11. A method for measuring hydrogen sulfide in a sample, which comprises reacting an aniline derivative represented by the general formula (I):

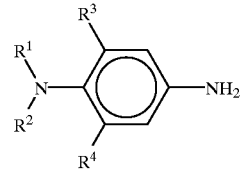

wherein $R^1$ and $R^2$ independently represent an unsubstituted $C_2-C_6$ alkyl group or a $C_2-C_6$ alkyl group substituted with at least one substituent each selected from the group consisting of a sulfo group, a sulfonate group, a carbamoyl group, and a substituted amino group, and $R^3$ and $R^4$ independently represent a hydrogen atom, a $C_1-C_6$ alkyl group or a halogen atom, and an oxidizing agent with hydrogen sulfide in a sample solution under an acidic condition, and colorimetrically analyzing the resulting solution;

with the proviso that when one of $R^3$ and $R^4$ is a hydrogen atom, and the other of $R^3$ and $R^4$ is a hydrogen atom or a methyl group, $R^1$ and $R^2$ are each a substituted $C_2$–$C_6$ alkyl group.

12. The method according to claim 11, wherein said substituent is a substituted amino group.

13. The method according to claim 11, wherein said oxidizing agent is ferric chloride, potassium ferricyanide, ammonium persulfate or potassium persulfate.

14. The method according to claim 11, wherein the aniline derivative is p-aminodi(3-sulfopropyl)aniline.

15. The method according to claim 11, wherein the aniline derivative is 4-amino-N,N-bis[2-(N',N'-dimethylamino)ethyl]aniline.

16. The method according to claim 11, wherein the aniline derivative is 4-amino-N,N-bis[2-(N',N'-diethylamino)ethyl]aniline.

17. The method according to claim 11, wherein the aniline derivative is 4-amino-2,6-dibromo-N,N-diethylaniline.

18. The method according to claim 11, wherein the aniline derivative is 4-amino-2,6-dibromo-N,N-dipropylaniline.

19. The method according to claim 11, wherein the aniline derivative is 4-amino-2,6-dichloro-N,N-diethylaniline.

20. The method according to claim 11, wherein the aniline derivative is 4-amino-2,6-dichloro-N,N-dipropylaniline.

* * * * *